United States Patent
Hirata

(10) Patent No.: US 10,251,981 B2
(45) Date of Patent: Apr. 9, 2019

(54) COATING LAYER, COATING SOLUTION, METHOD FOR FORMING COATING LAYER, AND METHOD FOR PRODUCING MEDICAL TOOL

(71) Applicant: KANEKA CORPORATION, Osaka-shi, Osaka (JP)

(72) Inventor: Masayuki Hirata, Settsu (JP)

(73) Assignee: Kaneka Corporation, Osaka-shi, Osaka (JP)

( * ) Notice: Subject to any disclaimer, the term of this patent is extended or adjusted under 35 U.S.C. 154(b) by 366 days.

(21) Appl. No.: 15/026,718

(22) PCT Filed: Sep. 25, 2014

(86) PCT No.: PCT/JP2014/075502
§ 371 (c)(1),
(2) Date: Apr. 1, 2016

(87) PCT Pub. No.: WO2015/050036
PCT Pub. Date: Apr. 9, 2015

(65) Prior Publication Data
US 2016/0250391 A1    Sep. 1, 2016

(30) Foreign Application Priority Data
Oct. 2, 2013 (JP) .................... 2013-207636

(51) Int. Cl.
| | | |
|---|---|---|
| C09D 175/04 | (2006.01) | |
| A61L 31/10 | (2006.01) | |
| C08G 18/36 | (2006.01) | |
| A61L 27/34 | (2006.01) | |
| A61L 29/08 | (2006.01) | |
| A61L 17/14 | (2006.01) | |
| C08G 18/62 | (2006.01) | |
| C08G 18/65 | (2006.01) | |
| C08G 18/40 | (2006.01) | |

(52) U.S. Cl.
CPC ............. *A61L 31/10* (2013.01); *A61L 17/145* (2013.01); *A61L 27/34* (2013.01); *A61L 29/085* (2013.01); *C08G 18/36* (2013.01); *C08G 18/4063* (2013.01); *C08G 18/622* (2013.01); *C08G 18/625* (2013.01); *C08G 18/65* (2013.01); *C09D 175/04* (2013.01); *A61L 2420/02* (2013.01)

(58) Field of Classification Search
CPC .................................................. C09D 175/04
See application file for complete search history.

(56) References Cited

U.S. PATENT DOCUMENTS

| | | | | |
|---|---|---|---|---|
| 4,329,490 A | * | 5/1982 | Williams ........... | C08G 18/3221 560/198 |
| 4,525,570 A | * | 6/1985 | Blum ................. | C08G 18/4009 528/44 |
| 4,876,126 A | * | 10/1989 | Takemura ............. | A61L 29/085 428/35.7 |
| 5,077,352 A | | 12/1991 | Elton | |
| 5,731,087 A | | 3/1998 | Fan et al. | |
| 5,891,109 A | | 4/1999 | Inoue et al. | |
| 6,020,071 A | | 2/2000 | Watson | |

FOREIGN PATENT DOCUMENTS

| | | | | |
|---|---|---|---|---|
| EP | 0747071 A1 | * | 12/1996 | .......... A61L 29/085 |
| JP | 60-259269 A | | 12/1985 | |
| JP | 1-195863 A | | 8/1989 | |
| JP | 4-227671 A | | 8/1992 | |
| JP | 5-76590 A | | 3/1993 | |
| JP | 5-168695 A | | 7/1993 | |
| JP | 8-33704 A | | 2/1996 | |
| JP | 8-337758 A | | 12/1996 | |
| JP | 10-52486 A | | 2/1998 | |
| JP | 10-57471 A | | 3/1998 | |
| JP | 10057471 A | * | 3/1998 | |
| JP | 10-231347 A | | 9/1998 | |
| JP | 11-114052 A | | 4/1999 | |
| JP | 11-506375 A | | 6/1999 | |
| JP | 2000-136347 A | | 5/2000 | |
| JP | 2000136347 A | * | 5/2000 | |
| JP | 2005-255966 A | | 9/2005 | |
| JP | 2010132735 A | * | 6/2010 | |
| JP | 2011-110393 A | | 6/2011 | |

OTHER PUBLICATIONS

International Search Report, issued in PCT/JP2014/075502, dated Dec. 9, 2014.
Written Opinion of the International Searching Authority, issued in PCT/JP2014/075502, dated Dec. 9, 2014.

\* cited by examiner

*Primary Examiner* — Cachet I Sellman
(74) *Attorney, Agent, or Firm* — Birch, Stewart, Kolasch & Birch, LLP

(57) ABSTRACT

Provided is a coating layer including a reaction product of a diisocyanate compound (a) selected from the group consisting of aromatic diisocyanates, aliphatic diisocyanates, and alicyclic diisocyanates, a polyol (b), and a copolymer (c) having a functional group selected from the group consisting of carboxylic acid groups, carboxylic acid ester groups, and carboxylic acid anhydride groups. The coating layer exhibits sufficient lubricity in wet conditions and has excellent durability.

11 Claims, No Drawings

COATING LAYER, COATING SOLUTION, METHOD FOR FORMING COATING LAYER, AND METHOD FOR PRODUCING MEDICAL TOOL

TECHNICAL FIELD

The present invention relates to a coating layer having excellent durability and exhibiting excellent lubricity in wet conditions, a coating solution for forming the coating layer, a method for forming the coating layer, and a method for producing a medical tool having a surface with the coating layer.

BACKGROUND ART

To the surface of a conventional medical tool having a portion to come in contact with a living body, a coating layer exhibiting lubricity in wet conditions has been applied by various techniques in order to reduce pains or damage to a living body due to the resistance at the time of contact. However, the conventional coating layer typically has a low affinity with materials constituting medical tools and unfortunately may be eluted or exfoliated in a living body.

The technique for overcoming such disadvantages is exemplified by the method that is disclosed in Patent Document 1 and includes ozone treatment of the surface of an object composed of a polymer material to form a functional group on the surface and graft polymerization of a hydrophilic polymer to the functional group and the method that is disclosed in Patent Document 2 and includes plasma treatment of the surface of an object. These methods however have problems of poor durability of the hydrophilic polymer and a reduction in mechanical properties of the object and are not preferred.

Patent Document 3 discloses a method of forming a coating layer having an interpenetrating network structure of a first polymer compound and a second polymer compound on the surface of an object by polymerizing a monomer in the presence of the first polymer compound having hydrophilicity to form the second polymer compound. The method however has problems of deterioration of the object and elution of residual monomers and oligomers.

Patent Document 4 discloses a method of forming a coating layer by using a urethane resin having a hydrophilic skeleton. The method prevents mechanical properties of an object from deteriorating but has problems of insufficient adhesiveness of the coating layer with an object and insufficient lubricity in wet conditions.

Patent Document 5 discloses a method of forming a coating layer by using a hydrophilic polyurethane having a block isocyanate with a terminal isocyanate group protected by a protective group. The method can solve the problems of Patent Document 4, however, has safety issues because a catalyst such as an amine and a heavy metal including tin is required to be used in order to form a urethane bond on an object. In addition, the method necessitates an increase in temperature, and this may affect the mechanical properties of an object or the profile of a medical tool. The method thus involves new problems to be solved.

Patent Document 6 discloses a method of forming a hydrophilic urethane coating layer by reacting a urethane compound containing a hydrophilic ethylene oxide on the surface of an object. In the method, the reaction rate is insufficient, and thus unreacted isocyanate is likely to cause the adhesion of the coating layers to each other or the adhesion between the coating layer and a package. In order to prevent the adhesion, heating or curing for a long period of time is required, but such treatment is undesirable from the viewpoint of the effect on the performance of an object and productivity. Use of a reaction catalyst in order to suppress the effect on the performance of an object or the reduction in productivity causes a problem of affecting biological safety.

Patent Document 7 discloses a method of bonding a coating layer composed of a maleic anhydride copolymer to the surface of a resin object through covalent bonds. In the method, a coating solution containing a maleic anhydride copolymer is applied to the surface of a resin object, and then the coating is required to be treated at a high temperature of 101 to 220° C. for a long period of time. This causes problems of the deterioration of mechanical properties of an object and of affecting the profile of a medical tool due to thermal degradation, for example.

Patent Document 8 discloses a method of forming a coating layer composed of a mixture of a maleic anhydride polymer substance and polyurethane having an allophanate bond on the surface of a resin object. The method uses a decomposition reaction of the allophanate bond of the polyurethane to crosslink the polyurethane with the maleic anhydride polymer substance, thus necessitates the treatment at a high temperature of 120 to 140° C., and has a problem of the deterioration of mechanical properties of an object.

Patent Document 9 discloses a coating solution for forming a coating exhibiting lubricity in wet conditions on the surface of a medical tool. The coating solution contains a hydrophilic polymer exhibiting lubricity in wet conditions, such as polyurethane, and a binder copolymer having a vinyl moiety and a carboxylic acid moiety. According to Example C-1 in Patent Document 9, the coating exhibiting lubricity in wet conditions prepared by using a vinyl ether/maleic anhydride copolymer (trade name: Gantrez (trademark) AN119) as the binder copolymer has insufficient durability against abrasion.

Patent Document 10 discloses a coating solution for forming a coating exhibiting lubricity in wet conditions on the surface of a medical tool. The coating solution is prepared by dissolving a methyl vinyl ether/maleic anhydride copolymer, a thermoplastic polyurethane (trade name: Tecoflex) synthesized by using an aliphatic isocyanate as a raw material, and a polyol such as polypropylene glycol as a crosslinking agent in an organic solvent such as tetrahydrofuran. However, the coating solution is required to be stored at 20° C. or less before application to the surface of a medical tool. It is thus supposed that each component contained in the coating solution has very high reactivity and a reaction product of the components has insufficient adhesiveness with the surface of a medical tool, for example.

CITATION LIST

Patent Literatures

Patent Document 1: JP-A No. H05-76590
Patent Document 2: JP-A No. H05-168695
Patent Document 3: JP-A No. H08-33704
Patent Document 4: JP-T No. H11-506375
Patent Document 5: JP-A No. H10-231347
Patent Document 6: JP-A No. H04-227671
Patent Document 7: JP-A No. 2005-255966
Patent Document 8: JP-A No. H10-52486
Patent Document 9: JP-A No. H08-337758
Patent Document 10: JP-A No. H11-114052

SUMMARY OF INVENTION

Technical Problem

An object of the present invention is to provide a coating layer exhibiting sufficient lubricity in wet conditions and having excellent durability, a coating solution for forming the coating layer, a method for forming a coating layer by using the coating solution, and a method for producing a medical tool having the coating layer.

Solution to Problem

As a result of intensive studies in such circumstances, the inventor of the present invention have found that by using a copolymer having a functional group selected from the group consisting of carboxylic acid groups, carboxylic acid ester groups, and carboxylic acid anhydride groups together with a diisocyanate compound and a polyol as crosslinking components for forming a coating layer, an appropriate crosslinked structure can be formed, and accordingly a coating layer exhibiting more excellent lubricity in wet conditions and having more excellent durability at high levels than those of conventional coating layers can be formed, and have completed the present invention.

That is, the present invention provides the coating layer in the following aspects [1] to [7], the coating solution in the aspects [8] to [16], the method for forming a coating layer in the aspects [17] to [19], and the method for producing a medical tool in the aspect [20].

[1] A coating layer including a reaction product of a diisocyanate compound (a) selected from the group consisting of aromatic diisocyanates, aliphatic diisocyanates, and alicyclic diisocyanates, a polyol (b), and a copolymer (c) having a functional group selected from the group consisting of carboxylic acid groups, carboxylic acid ester groups, and carboxylic acid anhydride groups.

[2] The coating layer of the aspect [1], in which the reaction product contains the component (a) in an amount of 0.01 to 50% by weight, the component (b) in an amount of 0.01 to 30% by weight, and the component (c) in an amount of 40 to 99% by weight.

[3] The coating layer of the aspect [1] or [2], in which the number of moles of all isocyanate groups in the component (a) is larger than the number of moles of all hydroxy groups in the component (b).

[4] The coating layer of any one of the aspects [1] to [3], in which the component (c) is a copolymer containing a maleic anhydride unit having a maleic anhydride group.

[5] The coating layer of any one of the aspects [1] to [4], in which the component (c) is a vinyl ether/maleic anhydride copolymer containing a vinyl ether unit and a maleic anhydride unit having a maleic anhydride group.

[6] The coating layer of any one of the aspects [1] to [5], in which in the component (c), at least a part of the carboxylic acid ester group and the carboxylic acid anhydride group is converted into the carboxylic acid group.

[7] The coating layer of the aspect [6], in which 1 mol % or more and 100 mol % or less of the total amount of the carboxylic acid ester group and the carboxylic acid anhydride group is converted into the carboxylic acid group.

[8] A coating solution including a diisocyanate compound (a) selected from the group consisting of aromatic diisocyanates, aliphatic diisocyanates, and alicyclic diisocyanates, a polyol (b), and a copolymer (c) having a functional group selected from the group consisting of carboxylic acid groups, carboxylic acid ester groups, and carboxylic acid anhydride groups.

[9] The coating solution of the aspect [8], in which the coating solution contains the component (a) in an amount of 0.01 to 50% by weight relative to the total amount of all components, the component (b) in an amount of 0.01 to 30% by weight relative to the total amount of all components, and the component (c) in an amount of 40 to 99% by weight relative to the total amount of all components. In the present specification, the total amount of all components means the total weight of all components except solvents contained in the coating solution.

[10] The coating solution of the aspect [8] or [9], in which the number of moles of all isocyanate groups in the component (a) is larger than the number of moles of all hydroxy groups in the component (b).

[11] The coating solution of any one of the aspects [8] to [10], in which the component (c) is a copolymer containing a maleic anhydride unit having a maleic anhydride group.

[12] The coating solution of any one of the aspects [8] to [11], in which the component (c) is a vinyl ether/maleic anhydride copolymer containing a vinyl ether unit and a maleic anhydride unit having a maleic anhydride group.

[13] The coating solution of any one of the aspects [8] to [12], in which the coating solution contains a prepolymer prepared by previously reacting at least some of the component (a) with at least some of the component (b) or the component (c).

[14] The coating solution of any one of the aspects [8] to [13], in which in the component (c), at least a part of the carboxylic acid ester group and the carboxylic acid anhydride group is converted into the carboxylic acid group.

[15] The coating solution of the aspect [14], in which 1 mol % or more and 100 mol % or less of the total amount of the carboxylic acid ester group and the carboxylic acid anhydride group is converted into the carboxylic acid group.

[16] The coating solution of any one of the aspects [8] to [15], in which the coating solution is a non-aqueous solution.

[17] A method for forming a coating layer, the method including applying the coating solution of any one of the aspects [8] to [16] to at least a part of an object, and drying the coating.

[18] The method for forming a coating layer of the aspect [17], in which the coating solution having a solution temperature of 40° C. or less is applied to the object.

[19] A method for forming a coating layer, the method including treating a surface of a coating layer formed by the method for forming a coating layer of the aspect [17] or [18] with an aqueous alkali solution, and then drying the surface.

[20] A method for producing a medical tool, the method including forming a coating layer on at least a part of an object for a medical tool by the method for forming a coating layer of any one of the aspects [17] to [19].

Advantageous Effects of Invention

The present invention enables the formation of a coating layer exhibiting sufficient lubricity in wet conditions and having excellent durability by a simple method.

DESCRIPTION OF EMBODIMENTS

The present invention will now be described in detail.
[Coating Layer]
The coating layer of the present invention is characterized by including a reaction product of a diisocyanate compound (a) selected from the group consisting of aromatic diisocyanates, aliphatic diisocyanates, and alicyclic diisocyanates, a polyol (b), and a copolymer (c) having a functional group selected from the group consisting of carboxylic acid groups, carboxylic acid ester groups, and carboxylic acid anhydride groups. The coating layer of the present invention is formed, for example, on an object, especially on at least a part of the surface of an object for a medical tool.

The coating layer of the present invention contains the reaction product prepared by reacting the components (a) to (c) in combination, and thus has good adhesiveness with various materials, especially with the surface of an object made from various resin materials, as well as has excellent lubricity in wet conditions and excellent durability (particularly a performance of suppressing the increase in friction coefficient at the time of friction). Thus, for example, when the coating layer of the present invention is formed on the surface of an object for a medical tool, pains and damage to a living body due to the resistance at the time of contact are significantly reduced, and the elution and exfoliation of the coating layer in a living body are significantly suppressed.

The reaction product itself constituting the coating layer of the present invention exhibits excellent adhesiveness with various materials, especially with various resin materials. Accordingly, by simply bringing a solution containing the reaction product into contact with the surface of an object or simply applying the solution to the surface, the coating layer of the present invention having the above-mentioned preferred properties can be formed without the synthesis of a reaction product by reacting the components (a) to (c) on the surface of an object under heat or without heating of the reaction product on the surface of an object at a high temperature. Consequently, even when formed on the surface of an object, the coating layer of the present invention achieves such advantages that the deterioration of mechanical properties and other controlled properties (for example, orientation properties) of the object, the deformation of the object, or the deterioration of the profile of a medical tool produced by forming the coating layer is not substantially caused, for example.

As specifically described later in the coating solution section, the components (a) to (c) are smoothly reacted at a comparatively low temperature of about 10 to 85° C. Thus, even when the reaction is performed on the surface of an object, the deterioration of mechanical properties and other controlled properties, the deformation of the object, and the deterioration of the profile of a medical tool are significantly suppressed, for example.

In the coating layer of the present invention, at least one diisocyanate compound (a) selected from the group consisting of aromatic diisocyanates, aliphatic diisocyanates, and alicyclic diisocyanates is used as the component (a). The diisocyanate compound (a) typically contains two isocyanate groups as the functional group per molecule.

Examples of the aromatic diisocyanate include 2,4-tolylene diisocyanate, 2,6-tolylene diisocyanate, 4,4'-diphenylmethane diisocyanate, p-phenylene diisocyanate, 3,3'-dimethylphenyl-4,4'-diisocyanate, m-xylylene diisocyanate, dianisidine diisocyanate, m-xylene diisocyanate, tetramethylxylene diisocyanate, and 1,5-naphthalene diisocyanate. The aromatic diisocyanates can be used singly or in combination of two or more of them.

Examples of the aliphatic diisocyanate include trans-vinylene diisocyanate, 2,2,4-trimethylhexamethylene diisocyanate, lysine diisocyanate, and 1,6-hexamethylene diisocyanate. The aliphatic diisocyanates can be used singly or in combination of two or more of them.

Examples of the alicyclic diisocyanate include trans-1,4-cyclohexane diisocyanate, cis-1,4-cyclohexane diisocyanate, 4,4'-dicyclohexylmethane diisocyanate, and isophorone diisocyanate. The alicyclic diisocyanates can be used singly or in combination of two or more of them.

Among these diisocyanate compounds (a), the aromatic diisocyanates are particularly preferred from the viewpoint of reactivity of capable of promoting crosslinking reaction at a temperature of 100° C. or less. The aliphatic diisocyanates and the alicyclic diisocyanates are particularly preferred from the view point that coloring of the coating layer after curing is easily suppressed. The diisocyanate compounds (a) can be used singly or in combination of two or more of them.

In the reaction product contained in the coating layer of the present invention, the content of the diisocyanate compound (a) is preferably 0.01% by weight to 50% by weight, more preferably 0.01% by weight to 30% by weight, and even more preferably 0.05% by weight to 15% by weight relative to the total amount of the reaction product. If the content of the diisocyanate compound (a) is less than 0.01% by weight, the coating layer is likely to have lower adhesiveness with an object or lower durability at the time of friction. If the content of the diisocyanate compound (a) is more than 50% by weight, the coating layer is likely to be brittle.

In the coating layer of the present invention, a polyol (hereinafter also called "polyol compound (b)") is used as the component (b). The polyol is a compound having two or more hydroxy groups.

In the present invention, use of the polyol compound (b) as an essential component enables a marked improvement in the durability of the coating layer, especially in the suppression performance of the increase of friction coefficient at the time of friction, for example. Although unclear at the present time, the reason why the durability of the coating layer and the like are improved is supposed as follows: The polyol compound (b) is used to crosslink to the component (a) or the component (c) and forms a three-dimensional structure. Accordingly, the component (a), the component (b), or the component (c) is firmly bonded, and unreacted components or decomposed components are prevented from flowing out from the coating layer in wet conditions. The durability is consequently improved.

In the present invention, the polyol compound (b) may be any bifunctional or higher functional polyol compound having two or more hydroxy groups, and exemplified by bifunctional polyol compounds having two hydroxy groups, such as ethylene glycol, polyethylene glycol, 1,6-hexanediol, and polytetramethylene glycol; and substantially trifunctional or higher functional polyol compounds having more than two hydroxy groups, such as branched derivatives of high molecular polyols, castor oil and derivatives thereof, glycerol, trimethylolpropane, trimethylolethane, 1,2,6-hexanetriol, pentaerythritol, sorbitol, and mannitol.

Examples of the branched derivative of a high molecular polyol include polyester polyols; polyether polyols such as poly(oxypropylene ether) polyol, poly(oxyethylene-propylene ether) polyol, and polytetramethylene glycol; and acrylic polyols. The branched derivative of a high molecular polyol preferably has a number average molecular weight of 200 or more and 40,000 or less, more preferably 200 or more and 5,000 or less, and even more preferably 200 or more and 3,000 or less from the viewpoint of the adhesiveness of the coating layer with an object and flexibility, for example. If the number average molecular weight is more than 40,000, the coating layer is likely to have lower adhesiveness with an object, and if the number average molecular weight is less than 200, the coating layer is likely to have lower flexibility. The number average molecular weight is a value determined by gel permeation chromatography (GPC) from molecular weight distribution in terms of polystyrene.

In the present invention, the polyol compounds (b) can be used singly or in combination of two or more of them, and at least one compound selected from the group consisting of bifunctional polyol compounds and trifunctional or higher functional compounds can be preferably used. Trifunctional or higher functional polyol compounds are preferred from the viewpoint that the formation of the three-dimensional structure is further promoted and the durability and the lubricity of a coating layer to be obtained are particularly achieved at high levels in a well-balanced manner. From the viewpoint of reactivity and handleability, a polyol compound having a primary alcohol as the terminal group, such as polytetramethylene glycol is preferred.

The component (a) and the component (b) are preferably contained in such an amount that the number of moles of all isocyanate groups of the diisocyanate compound as the component (a) is larger than the number of moles of all hydroxy groups of the polyol compound as the component (b). When the reaction rate of the isocyanate group in the component (a) with the component (c) is higher than that of the hydroxy group in the component (b) with the component (c), a coating layer to be obtained is likely to have more excellent durability and lubricity, for example.

In the reaction product contained in the coating layer of the present invention, the content of the polyol compound (b) is preferably 0.01% by weight to 30% by weight, more preferably 0.05% by weight to 15% by weight, and even more preferably 0.3% by weight to 13% by weight relative to the total amount of the reaction product. If the content of the polyol compound (b) is less than 0.01% by weight, the coating layer is likely to have lower adhesiveness with an object and lower durability at the time of friction. If the content of the polyol compound (b) is more than 30% by weight, the coating layer is likely to be sticky and to cause tacking.

In the coating layer of the present invention, a copolymer (hereinafter also simply called "copolymer (c)") having at least one functional group selected from the group consisting of carboxylic acid groups, carboxylic acid ester groups, and carboxylic acid anhydride groups is used as the component (c).

In the reaction product contained in the coating layer of the present invention, the content of the copolymer (c) is preferably 40% by weight to 99% by weight, more preferably 60% by weight to 98.5% by weight, and even more preferably 70% by weight to 98% by weight relative to the total amount of the reaction product. If the content of the component (c) is less than 40% by weight, the coating layer is likely to have lower lubricity. If the content of the component (c) is more than 99% by weight, the coating layer is likely to have lower lubricity and lower durability at the time of friction, for example.

Examples of the copolymer (c) include copolymers having a carboxylic acid group, copolymers having a carboxylic acid ester group, and copolymers having a carboxylic acid anhydride group (i.e., acid anhydride group). Specific examples of the copolymer having a carboxylic acid group include copolymers containing a carboxylic acid group-containing unit such as an acrylic acid unit, a methacrylic acid unit, a vinylbenzoic acid unit, a maleic acid unit, and a vinylphthalic acid unit. Specific examples of the copolymer having a carboxylic acid ester group include copolymers containing a carboxylic acid ester group-containing unit such as an acrylic ester unit, a methacrylic ester unit, a vinylbenzoic ester unit, a maleic ester unit, and a vinylphthalic ester unit. Specific examples of the copolymer having a carboxylic acid anhydride group include copolymers containing a carboxylic acid anhydride group-containing unit such as a maleic anhydride unit and a phthalic anhydride unit. In addition, a copolymer having two or more functional groups selected from the group consisting of carboxylic acid groups, carboxylic acid ester groups, and carboxylic acid anhydride groups can be used as the copolymer (c). The copolymers (c) can be used singly or in combination of two or more of them. The copolymer (c) is preferably at least one copolymer selected from the group consisting of copolymers having a carboxylic acid group; copolymers having a carboxylic acid ester group; copolymers having a carboxylic acid anhydride group; and copolymers having two or more functional groups selected from the group consisting of carboxylic acid groups, carboxylic acid ester groups, and carboxylic acid anhydride groups.

Among the copolymers (c), a copolymer containing at least a carboxylic acid anhydride unit having a carboxylic acid anhydride group is more preferred, and a copolymer containing a maleic anhydride unit having a maleic anhydride group (i.e., acid anhydride group) (hereinafter also simply called "maleic anhydride unit") is even more preferred from the viewpoint that the concentration of a carboxylic acid group per unit weight is easily increased and the durability and the lubricity of the coating layer are easily controlled. Examples of the copolymer containing a maleic anhydride unit include vinyl ether/maleic anhydride copolymers containing a vinyl ether unit and a maleic anhydride unit, vinyl acetate/maleic anhydride copolymers containing a vinyl acetate unit and a maleic anhydride unit, and styrene/maleic anhydride copolymers containing a styrene unit and a maleic anhydride unit. In the present invention, poly(maleic anhydride) containing only a maleic anhydride unit can be used in place of the copolymer containing a maleic anhydride unit.

In the coating layer of the present invention, among the above-mentioned copolymers containing a maleic anhydride unit, a vinyl ether/maleic anhydride copolymer composed of a vinyl ether unit and a maleic anhydride unit is specifically preferably used from the viewpoint of solubility in various solvents, hydrophilicity, and availability, for example. The vinyl ether unit is a divalent group derived from an olefinic compound such as alkyl vinyl ethers, alkylene vinyl ethers, and aromatic vinyl ethers. The maleic anhydride unit is a divalent group derived from maleic anhydride.

The vinyl ether/maleic anhydride copolymer may be any copolymer obtained by addition polymerization of an olefinic compound having a vinyl group with maleic anhydride, and is exemplified by alkyl vinyl ether/maleic anhydride copolymers such as methyl vinyl ether/maleic anhydride copolymers and ethyl vinyl ether/maleic anhydride copolymers; alkylene vinyl ether/maleic anhydride copolymers such as allyl vinyl ether/maleic anhydride copolymers and isobutylene ether/maleic anhydride copolymers; and aromatic vinyl ether/maleic anhydride copolymers such as phenyl ether/maleic anhydride copolymers. The vinyl ether/maleic anhydride copolymers can be used singly or in combination of two or more of them. Specifically, an alkyl vinyl ether/maleic anhydride copolymer is preferably used from the viewpoint of availability and an improvement in durability of the coating layer.

As for the copolymerization ratio of the vinyl ether unit and the maleic anhydride unit in the vinyl ether/maleic anhydride copolymer, the ratio of the maleic anhydride unit is preferably 40 to 60 mol % and more preferably 45 to 55 mol %, and the remainder is preferably the vinyl ether unit. If the copolymerization ratio of the maleic anhydride unit is less than 40 mol %, the coating layer is likely to have insufficient lubricity in wet conditions. If the copolymerization ratio of the maleic anhydride unit is more than 60 mol %, the coating layer has insufficient flexibility, and the coating layer is likely to exfoliate when a medical tool is bent. The copolymerization ratio can be calculated from the integrated ratio of any proton derived from vinyl ether and any proton derived from maleic anhydride in a proton NMR spectra.

The vinyl ether/maleic anhydride copolymer preferably has a weight average molecular weight of 2,000 to 5,000,000, more preferably 200,000 to 2,500,000, and even more preferably 1,000,000 to 2,000,000 from the viewpoint of hydrophilicity (lubricity) of the coating layer and film-thickness controllability when the coating layer is formed, for example. If the weight average molecular weight is less than 2,000, the coating layer is likely to have insufficient lubricity in wet conditions. If the weight average molecular weight is more than 5,000,000, the coating layer has higher water-holding capacity and higher lubricity, whereas a coating solution has higher solution viscosity, and this is likely to make it difficult to control the film thickness of the coating layer.

The copolymer (c) preferably has a carboxylic acid group before reaction with the diisocyanate compound (a), the polyol compound (b), or a prepolymer prepared by reacting at least some of the diisocyanate compound (a) and the polyol compound (b). When the copolymer (c) to undergo the reaction has only a carboxylic acid ester group and/or a carboxylic acid anhydride group, the carboxylic acid ester group or the carboxylic acid anhydride group is preferably converted into a carboxylic acid group, for example, by hydrolysis in advance. By converting a part of the carboxylic acid ester group or the carboxylic acid anhydride group into a carboxylic acid group, the reactivity with the isocyanate group in the component (a) is improved, and thus the crosslinking reaction is allowed to sufficiently proceed even when the coating solution is dried at a low temperature. Although the reason is unclear, the deterioration in lubricity of the coating layer arising from the adsorption of polyvalent ions in blood can be suppressed, and the durability can be improved.

When the copolymer (c) has a carboxylic acid ester group and/or a carboxylic acid anhydride group, all of or a part of the carboxylic acid ester group and the carboxylic acid anhydride group is preferably converted into a carboxylic acid group before reaction with the diisocyanate compound (a), the polyol compound (b), or a prepolymer prepared by reacting at least some of the diisocyanate compound (a) and the polyol compound (b). The lower limit for the conversion into a carboxylic acid group is preferably 1 mol % or more, more preferably 3 mol % or more, and even more preferably 5 mol % or more relative to the total amount of the carboxylic acid ester group and the carboxylic acid anhydride group. The upper limit for the conversion into a carboxylic acid group is preferably 100 mol % or less, more preferably 80 mol % or less, even more preferably 60 mol % or less, and particularly preferably 40 mol % or less relative to the total amount of the carboxylic acid ester group and the carboxylic acid anhydride group. In other words, the range of conversion into a carboxylic acid group is preferably 1 to 100 mol % (1 mol % or more and 100 mol % or less), more preferably 3 to 80 mol %, even more preferably 5 to 60 mol %, and particularly preferably 5 to 40 mol % relative to the total amount of the carboxylic acid ester group and the carboxylic acid anhydride group. In the present specification, the molar ratio (mol %) of a carboxylic acid ester group and/or a carboxylic acid anhydride group converted into a carboxylic acid group is also simply called "conversion ratio".

If the conversion into a carboxylic acid group is less than 1 mol % relative to the total amount of the carboxylic acid ester group and/or the carboxylic acid anhydride group, the coating layer is likely to have insufficient durability.

As the method of converting a carboxylic acid ester group and/or a carboxylic acid anhydride group into a carboxylic acid group, a common hydrolysis method can be used. The method is exemplified by a method of dissolving a copolymer (c) having a carboxylic acid ester group and/or a carboxylic acid anhydride group in a solvent, then adding required amounts of water and a catalyst, stirring the mixture, and removing impurities such as the solvent and the catalyst. In particular, as the method of converting a carboxylic acid anhydride group into a carboxylic acid group, a method of placing a copolymer (c) having a carboxylic acid anhydride group in such a container that the humidity and the temperature can be controlled, and exposing the copolymer (c) in predetermined humidity and temperature conditions for a predetermined period of time from the viewpoint of simplicity and easy control of the conversion ratio into a carboxylic acid group. In order to increase the conversion ratio into a carboxylic acid group in the method, a technique of increasing the humidity, a technique of increasing the temperature, and a technique of elongating the exposure time are exemplified, and two or more of the techniques can be combined.

In the present invention, the conversion ratio into a carboxylic acid group can be determined as follows: A copolymer (c) is subjected to $^1$H-NMR measurement (DMSO-$d_6$ solvent); and ½ of the number of moles of a carboxylic acid group calculated from a peak derived from the carboxylic acid group in the obtained chart is divided by the number of moles of a unit structure calculated from a peak derived from the unit structure having at least one group of a carboxylic acid group, a carboxylic acid ester group, and a carboxylic acid anhydride group. The conversion ratio in a coating solution is considered not to be changed from the conversion ratio in a solid state.

As described above, a preferred embodiment of the coating layer of the present invention contains the component (a) in an amount of 0.01 to 50% by weight, the component (b) in an amount of 0.01 to 30% by weight, and the component (c) in an amount of 40 to 99% by weight. In the preferred embodiment, the content of the component (a) can be changed from 0.01 to 50% by weight to 0.01 to 30% by weight or 0.05 to 15% by weight, the content of the component (b) can be changed from 0.01 to 30% by weight to 0.05 to 15% by weight or 0.3 to 13% by weight, and the content of the component (c) can be changed from 40 to 99% by weight to 60 to 98.5% by weight or 70 to 98% by weight. One of the contents of the components (a) to (c) may be changed, or two or more of the contents of the components (a) to (c) may be changed.

The coating layer of the present invention can contain compounding agents commonly used in the field in addition to the components (a) to (c) and the solvents contained in the coating solution described later to such an extent that the preferred properties are not impaired. Examples of the compounding agent include pharmaceutical components, anticoagulant agents, disintegrants, absorption promoters for pharmaceutical components, plasticizers, stabilizers, radiation absorbers, and polymer compounds other than the above. The compounding agents can be used singly or in combination of two or more of them. On the surface of the coating layer of the present invention, hydrophobic oil such as silicone oil and functionalized silicone oils can be further applied as an antiblocking agent.

The coating layer of the present invention may have any thickness. When used for medical tools, the coating layer preferably has a thickness of 0.1 to 30 µm, more preferably 0.5 to 10 µm, and even more preferably 0.5 to 5 µm. If the coating layer has a thickness of less than 0.1 µm, the coating layer is likely to have lower lubricity or lower durability at the time of friction. If the coating layer has a thickness of more than 30 µm, larger amounts of components are likely to be eluted in a liquid such as blood.

[Coating Solution]

The coating solution of the present invention will next be described in detail. The coating solution of the present invention contains a diisocyanate compound (a), a polyol compound (b), and a copolymer (c). Use of the coating solution of the present invention enables easy production of the coating layer of the present invention having the above-mentioned preferred properties on the surface of an object (especially an object for a medical tool).

When a conventional coating solution is used and a reaction product obtained by polymerization reaction of components contained therein is applied to the surface of an object, it is difficult to yield a coating layer having durability required for medical tools or other objects and having adhesiveness with the surface of an object, and polymerization reaction is required on the surface of an object. However, to promote the polymerization reaction, heating at a comparatively high temperature is necessitated, for example, and this causes the deterioration of the mechanical properties and other controlled properties (for example, orientation properties) of an object, the deformation of an object, or other defects. The conventional coating solutions are thus applied to a greatly limited range.

In contrast, the coating solution of the present invention contains the components (a) to (c) in combination, and thus has such an advantage that the components (a) to (c) can be polymerized at a comparatively low heating temperature of about 10 to 85° C. Hence, even when the coating solution of the present invention is applied to the surface of an object and the components (a) to (c) are polymerized to synthesize a reaction product, the deterioration of the mechanical properties and other controlled properties (for example, orientation properties) of the object, the deformation of the object, and the deterioration of the profile of an end product such as a medical tool produced by forming the coating layer on the surface of an object for a medical tool are significantly suppressed, for example.

The coating solution of the present invention contains the same diisocyanate compound (a), the same polyol compound (b), and the same copolymer (c) as those in the coating layer of the present invention and can further contains a solvent. The diisocyanate compound (a) can be one compound or two or more compounds selected from the same compounds as the diisocyanate compounds (a) exemplified in the coating layer section, and preferred compounds are also the same. The polyol compound (b) can be one compound or two or more compounds selected from the same compounds as the polyol compounds (b) exemplified in the coating layer section, and preferred compounds are also the same. The copolymer (c) can be one compound or two or more compounds selected from the same compounds as the copolymers (c) exemplified in the coating layer section, and preferred compounds are also the same.

In the coating solution of the present invention, the content of the component (a) is preferably 0.01 to 50% by weight relative to the total amount of all components, the content of the component (b) is preferably 0.01 to 30% by weight relative to the total amount of all components, and the content of the component (c) is preferably 40 to 99% by weight relative to the total amount of all components. When the coating solution of the present invention contains a solvent, the total amount of all components is a total weight of all components except the solvent. The more preferred ranges and the even more preferred ranges of the contents of the components (a) to (c) are the same as those for the coating layer, and the reason of the numerical limitation of the content is also the same as that for the coating layer.

In the coating solution of the present invention, the content of the component (a) can be changed from 0.01 to 50% by weight to 0.01 to 30% by weight or 0.05 to 15% by weight, the content of the component (b) can be changed from 0.01 to 30% by weight to 0.05 to 15% by weight or 0.3 to 13% by weight, and the content of the component (c) can be changed from 40 to 99% by weight to 60 to 98.5% by weight or 70 to 98% by weight. One of the contents of the components (a) to (c) may be changed, or two or more of the contents of the components (a) to (c) may be changed.

The coating solution of the present invention may contain a prepolymer obtained by previously reacting at least some of the respective components (a) to (c). The at least some of the respective components (a) to (c) are at least some of the total contents of the respective components (a) to (c).

The prepolymer is exemplified by a prepolymer A prepared by reacting at least some of the component (a), at least some of the component (b), and at least some of the component (c), a prepolymer B prepared by reacting at least some of the component (a) and at least some of the component (b), and a prepolymer C prepared by reacting at least some of the component (a) and at least some of the component (c). Among these prepolymers, the prepolymers B and C are preferred from the viewpoint of an improvement in hydrophilicity (lubricity) or durability of the coating layer.

The amounts of the component (a), the component (b), and the component (c) used for the synthesis of the prepolymers A to C may be any range as long as the coating layer of the present invention having intended properties can be obtained, however, the content of the component (a) is preferably 0 to 100% by weight relative to the total amount of the component (a), the content of the component (b) is preferably 0 to 75% by weight relative to the total amount of the component (b), and the content of the component (c) is preferably 0 to 50% by weight relative to the total amount of the component (c).

For example, the weight ratio (a)/(b) of the component (a) and the component (b) used for the synthesis of the prepolymer B is preferably in a range from 3/1 to 1/3. If the ratio of the component (b) exceeds the range, curing of the prepolymer B itself proceeds. Accordingly, the reaction rate of the isocyanate group of the component (a) with the component (c) decreases when the prepolymer B is reacted with the component (c), and thus the effect by the component (c) is likely to be insufficiently achieved. If the ratio of the component (b) is less than the range, the prepolymer B has excessively high reactivity and thus is likely to have lower handleability.

The weight ratio (a)/(c) of the component (a) and the component (c) used for the synthesis of the prepolymer C is preferably in a range from 3/1 to 1/5. If the ratio of the component (c) exceeds the range, the amount of the isocyanate group of the component (a) to be reacted with the component (b) decreases to reduce three-dimensional crosslinkages, and the coating layer finally obtained is likely to have lower durability, for example. If the ratio of the component (c) is less than the range, the prepolymer C has excessively high reactivity and thus is likely to have lower handleability.

When the prepolymer A is synthesized, the above ranges of the weight ratios (a)/(b) and (a)/(c) are preferably applied.

In the coating solution of the present invention, the addition order and the reaction order of the components (a) to (c) are not limited to particular orders, however, it is specifically preferred that the copolymer (c) be added to the prepolymer as the reaction product of the diisocyanate compound (a) and the polyol compound (b) and the whole be reacted to yield a reaction product from the viewpoint of easy availability of raw materials, for example. Materials produced by adding a small amount of the component (b) to the component (a), such as trade name: NIPPOLAN (manufactured by Nippon Polyurethane Industry Co., Ltd.), are commercially available and such commercial products can be suitably used.

The coating solution of the present invention can contain a solvent. The solvent is not limited to particular solvents, but is preferably a solvent without an active hydrogen that reacts with an isocyanate group from the viewpoint of prevention of the deterioration with time of the components (a) to (c), prepolymers, or other components and from the viewpoint of uniform dispersibility and reaction rate of the components (a) to (c). Examples of the solvent without an active hydrogen include acetonitrile, tetrahydrofuran (THF), acetone, and halogenated hydrocarbons such as dichloromethane and chloroform. Specifically preferred are non-aqueous solvents having appropriate affinity with the surface of an object and having a solubility parameter value $\delta$ of 8 to 13 $(cal/cm)^{1/2}$, and more preferred are nonaqueous solvents having a solubility parameter value $\delta$ of 9 to 12 $(cal/cm)^{1/2}$, such as tetrahydrofuran and acetone.

The coating solution of the present invention can contain various compounding agents commonly used in the field in addition to the components (a) to (c) and the solvents to such an extent that the preferred properties of the coating layer finally obtained are not impaired. Examples of the compounding agent include pharmaceutical components, anti-coagulant agents, disintegrants, absorption promoters for pharmaceutical components, plasticizers, stabilizers, radiation absorbers, and polymer compounds other than the above. The compounding agents can be used singly or in combination of two or more of them.

The coating solution of the present invention can be prepared, for example, by mixing the components (a) to (c). The coating solution of the present invention can also be prepared by reacting the components (a) to (c) to yield a reaction product. The coating solution of the present invention can also be prepared by mixing a prepolymer B prepared by reacting at least some of the component (a) and at least some of the component (b), with the remaining component (a), the remaining component (b), and the component (c). The coating solution of the present invention can also be prepared by mixing a prepolymer C prepared by reacting at least some of the component (a) and at least some of the component (c), with the remaining component (a), the remaining component (c), and the component (b). The coating solution of the present invention can also be prepared by mixing a prepolymer A prepared by reacting at least some of the respective components (a) to (c), with the remaining components (a) to (c). The coating solution of the present invention may be in such a form that a mixture of the mixture, the reaction product, or the prepolymer of the respective components and the remaining components is dissolved, dispersed, or suspended in a solvent, as necessary.

[Method for Forming Coating Layer]

The method for forming the coating layer exhibiting lubricity in wet conditions of the present invention may be any method capable of giving the coating layer of the present invention, and is exemplified by a method of bringing the above-mentioned coating solution (especially a coating solution containing a reaction product or a mixture of a prepolymer and remaining components) into contact with the surface of an object and allowing the surface of the object to adsorb the coating solution and a method of applying the coating solution to the surface of an object, allowing the resulting coating to stand, and, as necessary, drying the coating.

In terms of the uniformity of a coating layer to be formed and easy removal of solvents, preferred is a method of applying a coating solution prepared by dissolving a mixture or a reaction product of the components in a solvent, preferably in a volatile nonaqueous solvent (an organic solvent or a nonaqueous solvent) to the surface of an object. When a coating solution prepared by dissolving a reaction product in a volatile nonaqueous solvent is used, the coating layer having intended properties can be formed by simply applying the coating solution to the surface of an object. Needless to say, after the coating solution prepared by dissolving a reaction product is applied to the surface of an object, the coating may be heated. The method of applying the coating solution to the surface of an object may be any method for applying a liquid to the surface of a solid, and is exemplified by brush coating, roll coater coating, clip coating, spray coating, comma coating, knife coating, die coating, the coating, lip coating, and curtain coating.

The application speed of the coating solution to the surface of an object is not limited to particular values as long as the formed coating layer has no uneven coating or uneven thickness, and can be appropriately set depending on the form and formulation of the coating solution and the concentrations of all components. The coating solution is preferably applied to the surface of an object at a constant speed from the viewpoint that a uniform coating layer is easily obtained, for example.

The coating solution may have any solution temperature when applied to the surface of an object, however, the solution temperature is preferably low in terms of the stability of solution properties. For example, the temperature is preferably 40° C. or less, more preferably 30° C. or less, and even more preferably 20° C. or less. If having a solution temperature of more than 40° C., the coating solution has unstable solution properties and is likely to cause uneven coating and to become difficult to control the thickness of a coating layer. The lower limit of the solution temperature of the coating solution is preferably −10° C. or more in terms of hygroscopic properties of the coating solution, for example. The solution temperature range when the coating solution is applied to the surface of an object is preferably −10° C. to 40° C., more preferably −10° C. to 30° C., and even more preferably −10° C. to 20° C. The above description reveals that the coating solution of the present invention can be applied at about room temperature throughout the year.

The drying temperature and the drying time for drying a coating formed from the coating solution of the present invention are not limited to particular values. For example, the drying is performed preferably at a temperature of about 10 to 85° C. and more preferably about 20 to 60° C. and preferably for about 0.1 to 5 hours and more preferably about 0.5 to 2 hours. Even when the drying is performed at such a comparatively low temperature, the components (a) to (c) in the coating solution can be sufficiently reacted to yield the reaction product having intended properties, and thus the coating layer of the present invention can be formed without the deterioration of mechanical properties or the deformation of an object, for example. When an object has high heat resistance and the like, the drying may be performed at a higher temperature than the above-mentioned drying temperature.

The reaction method by adding the diisocyanate compound (a), the polyol compound (b), and the copolymer (c) may be any method capable of yielding the reaction product having intended properties. However, if the components (a) to (c) are insufficiently reacted during the formation of the coating layer, the formed coating layer contains remaining isocyanate groups, and this may cause the sticking or adhesion of the coating layers to each other or the sticking or adhesion between an object on which the coating layer is formed and a package or a protection member. To address this, the reaction is particularly preferably performed in a solvent system from the viewpoint of suppression of insufficient reaction, reaction rate, and uniform dispersibility of the components (a) to (c). In other words, a coating solution containing a solvent is preferably used to perform the reaction. The solvent used in the coating solution is preferably an organic solvent without an active hydrogen that reacts with an isocyanate group. Such a solvent can be exemplified by acetonitrile, THF, acetone, and halogenated hydrocarbons such as dichloromethane and chloroform.

In order to effectively deactivate remaining isocyanate groups, a compound having an active hydrogen (hereinafter called "active hydrogen compound"), preferably a low molecular weight active hydrogen compound can be added after substantial completion of the reaction of the components (a) to (c) in the coating solution. The time after substantial completion of the reaction means such a state that almost all the functional groups that can be theoretically reacted have been completely reacted on the basis of the numbers of the respective functional groups of the components (a) to (c) contained in the coating solution. This expression also includes such a case that an excess amount of a functional group over a required amount of the functional group for giving intended properties is introduced to a system and a compound having an active hydrogen is added during the reaction. However, this method is difficult to control the reaction in many cases and is not so preferred.

Examples of the active hydrogen compound include alcohols, amines, carboxylic acids, and water. Specifically, alcohols, amines, carboxylic acids, and the like are preferred from the viewpoint of suppression of reductions of the lubricity and the stability of the coating solution arising from, for example, foaming by the urea bond formation and the formation of insoluble urea, and alcohols are more preferred from the viewpoint of safety. Examples of the alcohol include alkyl alcohols such as methanol, ethanol, and isopropanol and polyols such as glycerol and pentaerythritol.

The measurement method of the amount of the remaining isocyanate does not particularly affect the present invention, and an existing technique can be used. For example, the titration method in accordance with ASTM D1638-74 can be exemplified.

In order to further improve the lubricity of the coating layer in wet conditions, it is preferable that the coating solution be applied to an object and dried, the reaction of the components (a), (b), and (c) be substantially completed to form a coating layer, and then the coating layer be brought into contact with an aqueous alkali solution to be treated.

It is supposed that by the treatment with an aqueous alkali solution, a carboxylic acid ester group and a carboxylic acid anhydride group derived from the component (c) and remaining in the coating layer are hydrolyzed to form a carboxylic acid group, and accordingly excellent lubricity can be achieved in wet conditions. The usable aqueous alkali solution is not limited to particular solutions, however, an aqueous metal hydroxide solution is preferred. Examples of the aqueous metal hydroxide solution include aqueous solutions of alkali metal hydroxides such as sodium hydroxide and potassium hydroxide; and aqueous solutions of alkaline earth metal hydroxides such as calcium hydroxide. Specifically, aqueous solutions of sodium hydroxide, potassium hydroxide, and the like are preferred in terms of availability and easy achievement of improvement effect of the lubricity of a coating layer in wet conditions. In order to further improve the treatment effect with an aqueous alkali solution, the aqueous alkali solution may be warmed at about 30 to 50° C.

When a coating layer is formed, a coating solution containing all the diisocyanate compound (a), the polyol compound (b), and the copolymer (c) may be used for coating. Alternatively, a urethane prepolymer solution prepared by previously reacting some or all of the diisocyanate compound (a) and the polyol compound (b) may be applied, and then remaining components may be applied to the surface of the formed layer to be infiltrated into the layer, giving the coating layer. In terms of simplicity of the process, it is preferable that a coating solution containing all the diisocyanate compound (a), the polyol compound (b), and the copolymer (c) be used to perform coating once or, as necessary, twice or more.

[Method for Producing Medical Tool]

The method for producing a medical tool of the present invention is characterized by forming the above-mentioned coating layer on at least a part of the surface of an object for a medical tool by the above-mentioned method for forming a coating layer. Here, the object for a medical tool can be a common medical tool used in contact with a body composition such as biological tissues and body fluids. Specific examples of the medical tool include, but are not necessarily limited to, blood bags, urine collection bags, blood transfusion sets, sutures, drain tubes, various catheters, blood access devices, blood circuits, artificial blood vessels, artificial kidneys, artificial heart-lung devices, artificial valves, plasma exchange membranes, various adsorbents, CAPD devices, IABP devices, pacemakers, artificial joints, head prosthesis, dental materials, intraocular lenses, soft contact lenses, and various shunts.

The material constituting the medical tools is not limited to particular materials. Preferably used are various elastomers such as polyalkylene elastomers, polyamide elastomers, and polyamide elastomers; thermoplastic resin materials such as polyester, polycarbonate, and polyvinyl chloride; and thermosetting resin materials such as polyurethane and silicone.

These medical tools may have a coating layer exhibiting lubricity in wet conditions on the whole surface or may have a coating layer exhibiting lubricity in wet conditions only on a part, for example, that comes in contact with a body composition such as biological tissues and body fluids. If desired, by controlling the concentration of a coating solution or the number of applications to change the coating amount, two or more coating layers can be formed so as to give two or more parts having different lubricities.

EXAMPLES

The present invention will be specifically described with reference to examples hereinafter, but the invention is not intended to be limited to the examples. In examples and comparative examples, "part" represents "part by weight" and "%" represents "% by weight" unless otherwise stated.

The abbreviations in the below description represent the following substances.

4,4'-MDI: 4,4'-diphenylmethane diisocyanate
1,6-HDI: 1,6-hexamethylene diisocyanate The object for a medical tool used in the examples was a tube having an outer diameter of 1 mm and a length of 200 mm and prepared by connecting a tube (elastomer portion) made from a polyamide elastomer resin (Pebax: trademark, a polyether block amide copolymer, manufactured by Elf Atochem) to a tube (nylon portion) made from nylon 12.

Measurements and evaluations in examples and comparative examples were performed in the following conditions and procedures.

[Evaluation of Durability]

In a bovine blood mixed with heparin at a proportion of 20 iu/ml, a tube (coated tube) having the coating layer prepared in each of Examples 1 to 48 and Comparative Examples 1 to 6 was immersed for 2.0 hours, and then the bovine blood attached to the tube surface was washed in physiological saline. Each tube was rubbed by hand twenty strokes or more. The slidability and the appearance of the coating layer were observed and evaluated on the basis of the following criteria. As control samples, a coated tube (control 1) that was not immersed in a bovine blood and a sample (control 2) that was not coated but immersed in a bovine blood were also subjected to the same operation, and the difference of existence of the immersion in a bovine blood was observed.

The evaluation of durability was performed on the elastomer portion and the nylon portion, separately.

⊚: A sample maintained good slidability that was substantially the same as that of control 1 and better than that of control 2.

o: A sample maintained good slidability that was slightly inferior to that of control 1 but was better than that of control 2.

Δ: A sample had substantially the same slidability as that of control 2.

[Appearance]

The coating layer condition was visually observed.

o: No uneven coating or whitening is observed on a coating layer.

Δ: Slight uneven coating or whitening is observed on a coating layer.

x: Marked uneven coating or whitening is observed on a coating layer.

[Conversion Ratio of Vinyl Ether/Maleic Anhydride Copolymer into Carboxylic Acid Group]

In 0.6 ml of deuterated DMSO (DMSO-$d_6$), 1 mg to 10 mg of vinyl ether/maleic anhydride copolymer was dissolved and then subjected to $^1$HNMR spectrum measurement. The conversion ratio was calculated from the obtained chart in accordance with the following expression.

Conversion ratio (%)=[(α/2)/(ß/2×maleic anhydride copolymerization ratio)]×100

α: An integrated value of a peak derived from a carboxylic acid group (ring-opening of 1 mol of a carboxylic acid anhydride group gives 2 mol of a carboxylic acid group)

ß: The sum of the integrated value of a peak derived from methylene ($CH_2$) of a vinyl ether unit structure and the integrated value of peaks derived from methine (H×2) of unconverted and converted maleic anhydride unit structures.

Maleic anhydride copolymerization ratio: 0.5 (50% due to an alternating copolymer)

Synthesis Example 1

(1) Preparation of Coating X Solution

In a 1-L recovery flask, a diisocyanate compound (a) and dehydrated tetrahydrofuran (THF) were placed at proportions (parts) shown in Table 1, and the temperature was increased to 50° C. while the whole was stirred under a stream of nitrogen. While the reaction mixture was continuously stirred under a stream of nitrogen, a polyol compound (b) was added at a proportion (parts) shown in Table 1 to the reaction mixture in the flask. The resulting mixture was further stirred at 50° C. for 5 hours, giving coating X solutions (X1 to X3) as urethane prepolymer solutions prepared by reacting the component (a) and the component (b).

The time of addition of the polyol compound (b) to the reaction mixture was 2 hours when the polyol compound (b) was 1,2,6-hexanetriol and was 3 hours when the polyol compound (b) was castor oil or 1,6-hexanediol.

TABLE 1

| | | Coating X solution | | |
|---|---|---|---|---|
| | | X1 | X2 | X3 |
| Diisocyanate compound (a) [parts] | 4,4'-MDI | | 23.5 | 25 |
| | 1,6-HDI | 12 | | |
| Polyol compound (b) [parts] | 1,2,6-Hexanetriol | 3 | | |
| | Castor oil | | 21.5 | |
| | 1,6-Hexanediol | | | 5 |
| Solvent [parts] | Dehydrated THF | 285 | 255 | 270 |

(2) Preparation of Coating Y Solution

Next, a vinyl ether/maleic anhydride copolymer (trade name: GANTREZ (trademark) AN-169, a weight average molecular weight of 2,000,000, manufactured by ISP Japan) or a vinyl ether/maleic anhydride copolymer (trade name: GANTREZ (trademark) AN-139, a weight average molecular weight of 1,000,000, manufactured by ISP Japan) was used as the component (c), and 0.5 parts, 1.0 part, or 2.0 parts of the component (c) was dissolved in 19.5 parts, 19.0 parts, or 18.0 parts of dehydrated THF as shown in Table 2, giving a coating Y solution (Y1, Y2, Y3, Y4, Y5, or Y6) as a 2.5%, 5.0%, or 10.0% solution of the vinyl ether/maleic anhydride copolymer. Each of the two copolymers was adjusted so as to give a conversion ratio to a carboxylic acid group of 1 to 5 mol % and used.

TABLE 2

| | | Y1 | Y2 | Y3 | Y4 | Y5 | Y6 |
|---|---|---|---|---|---|---|---|
| Vinyl ether/maleic anhydride copolymer [parts] | Weight average molecular weight of 2,000,000 | 0.5 | 1.0 | 2.0 | | | |
| | Weight average molecular weight of 1,000,000 | | | | 0.5 | 1.0 | 2.0 |
| | Dehydrated THF | 19.5 | 19.0 | 18.0 | 19.5 | 19.0 | 18.0 |

A vinyl ether/maleic anhydride copolymer (GANTREZ AN-169) powder was placed in such a glass container that the humidity and the temperature were controllable. While the humidity was maintained in a range from 40 to 80% and the temperature was maintained in a range from 40 to 80° C., the copolymer powder was exposed for 6 to 24 hours to perform ring-opening of a carboxylic acid anhydride group in such a way as to give a conversion ratio from a carboxylic acid anhydride group to a carboxylic acid group of 5 to 30 mol %, yielding a converted copolymer (c1). A converted copolymer (c2) having a conversion ratio of 5 to 30 mol % was obtained in the same manner as in the above except that the vinyl ether/maleic anhydride copolymer was changed from GANTREZ AN-169 to GANTREZ AN-139.

A converted copolymer (c3) having a conversion ratio from a carboxylic acid anhydride group to a carboxylic acid group of 60 to 70 mol % was obtained in the same manner as in the above except that the exposure time was changed from 6 to 24 hours to 60 to 80 hours in the ring-opening treatment of the vinyl ether/maleic anhydride copolymer (GANTREZ AN-169).

In the same manner as for the above Y1 to Y3 solutions, coating Y7, Y8, and Y9 solutions were obtained as 2.5%, 5.0%, and 10.0% solutions of the converted copolymer (c1) in dehydrated THF, coating Y10, Y11, and Y12 solutions were obtained as 2.5%, 5.0%, and 10.0% solutions of the converted copolymer (c2) in dehydrated THF, and coating Y13, Y14, and Y15 solutions were obtained as 2.5%, 5.0%, and 10.0% solutions of the converted copolymer (c3) in dehydrated THF, respectively.

Examples 1 to 3

As shown in Table 3, 5 parts of the coating X1 solution was added to 100 parts of the coating Y1, Y2, and Y3 solutions, giving coating Z1, Z2, and Z3 solutions. The solution temperatures of the obtained Z1, Z2, and Z3 solutions were adjusted to about 5° C. to 10° C. Then, a tube as the object for a medical tool was immersed in the Z1, Z2, or Z3 solution, and the solution was applied at a constant speed in parallel with a longitudinal direction of the tube. The coated tube was dried at 50° C. for 60 minutes. The tube after coating was immersed in a 0.1 to 1.0 N aqueous sodium hydroxide solution at room temperature for 30 seconds, and then was washed twice by immersion in RO water, giving a tube with a coating layer. The appearance and the durability of the obtained tubes were evaluated. Table 3 shows the results.

Examples 4 to 6

The coating X1 solution and the respective coating Y1, Y2, and Y3 solutions obtained in Synthesis Example 1 were used to prepare tubes with a coating layer. In other words, a tube as the object for a medical tool was immersed in the X1 solution, and the solution was applied at a constant speed in parallel with a longitudinal direction of the tube. The coated tube was dried at 55° C. for 60 minutes. Then, the tube coated with the X1 solution and dried was immersed in the Y1, Y2, or Y3 solution, and the solution was applied at a constant speed in parallel with a longitudinal direction of the tube. The coated tube was dried at 50° C. for 60 minutes. Next, the tube coated with the X1 solution and the Y1, Y2, or Y3 solution and dried was immersed in a 0.1 to 1.0 N aqueous sodium hydroxide solution at room temperature for 30 seconds, and then was washed twice by immersion in RO water, giving a tube with a coating layer. The appearance and the durability of the obtained tubes were evaluated. Table 3 shows the results.

Examples 7 to 9

Tubes with a coating layer were obtained in the same manner as in Examples 4 to 6 except that the drying temperature after application of the X1 solution to the tube in Examples 4 to 6 was changed from 55° C. to 25° C. The appearance and the durability of the obtained tubes were evaluated. Table 3 shows the results.

Examples 10 to 12

As shown in Table 3, 5 parts of the coating X2 solution was added to 100 parts of the coating Y1, Y2, and Y3 solutions, giving coating Z4, Z5, and Z6 solutions. The solution temperatures of the obtained Z4, Z5, and Z6 solutions were adjusted to about 30° C. Then, a tube as the object for a medical tool was immersed in the Z4, Z5, or Z6 solution, and the solution was applied at a constant speed in parallel with a longitudinal direction of the tube. The coated tube was dried at 80° C. for 60 minutes. The tube after coating was immersed in a 0.1 to 1.0 N aqueous sodium hydroxide solution at room temperature for 30 seconds, and then was washed twice by immersion in RO water, giving a tube with a coating layer. The appearance and the durability of the obtained tubes were evaluated. Table 3 shows the results.

Examples 13 to 15

The coating X2 solution and the respective coating Y1, Y2, and Y3 solutions obtained in Synthesis Example 1 were used to prepare tubes with a coating layer. In other words, a tube as the object for a medical tool was immersed in the X2 solution, and the solution was applied at a constant speed in parallel with a longitudinal direction of the tube. The coated tube was dried at 55° C. for 60 minutes. Then, the tube coated with the X2 solution and dried was immersed in the Y1, Y2, or Y3 solution, and the solution was applied at a constant speed in parallel with a longitudinal direction of the tube. The coated tube was dried at 50° C. for 60 minutes. Next, the tube coated with the X2 solution and the Y1, Y2, or Y3 solution and dried was immersed in a 0.1 to 1.0 N aqueous sodium hydroxide solution at room temperature for 30 seconds, and then was washed twice by immersion in RO water, giving a tube with a coating layer. The appearance and the durability of the obtained tubes were evaluated. Table 3 shows the results.

Examples 16 to 18

Tubes with a coating layer were obtained in the same manner as in Examples 13 to 15 except that the drying temperature after application of the X2 solution to the tube in Examples 13 to 15 was changed from 55° C. to 25° C. The appearance and the durability of the obtained tubes were evaluated. Table 3 shows the results.

Examples 19 to 21

To 100 parts of the coating Y4, Y5, and Y6 solutions, 5 parts of the coating X3 solution was added, giving coating Z7, Z8, and Z9 solutions. The solution temperatures of the obtained Z7, Z8, and Z9 solutions were adjusted to about −5° C. Then, a tube as the object for a medical tool was immersed in the Z7, Z8, or Z9 solution, and the solution was applied at a constant speed in parallel with a longitudinal direction of the tube. The coated tube was dried at 80° C. for 60 minutes. The tube after coating was immersed in a 0.1 to 1.0 N aqueous sodium hydroxide solution at room temperature for 30 seconds, and then was washed twice by immersion in RO water, giving a tube with a coating layer. The appearance and the durability of the obtained tubes were evaluated. Table 3 shows the results.

Comparative Examples 1 to 3

Tubes with a coating layer were obtained in the same manner as in Examples 1 to 3 except that only the treatment of applying the coating Y1, Y2, or Y3 solution to the tube and drying the tube at 100° C. for 60 minutes was performed in place of the treatment of applying the coating Z1, Z2, or Z3 solution to the tube and drying the tube at 55° C. for 60 minutes in Examples 1 to 3. The appearance and the durability of the obtained tubes were evaluated. Table 3 shows the results.

Examples 22 to 42 and Comparative Examples 4 to 6

Tubes with a coating layer were obtained in the same manner as in Examples 1 to 21 and Comparative Examples 1 to 3 except that each of the coating Y7 to Y12 solutions was used in place of the coating Y1 to Y6 solutions. The appearance and the durability of the obtained tubes were evaluated. Table 4 shows the results.

TABLE 3

| | | | | | | | | | Example | | | | | | |
|---|---|---|---|---|---|---|---|---|---|---|---|---|---|---|---|
| | | | | 1 | 2 | 3 | 4 | 5 | 6 | 7 | 8 | 9 | 10 | 11 | 12 | 13 |
| X Solution | Dehydrated THF solution of prepolymer of diisocyanate compound (a) and polyol compound (b) | | X1 | ○ | ○ | ○ | ○ | ○ | ○ | ○ | ○ | ○ | | | | |
| | | | X2 | | | | | | | | | | ○ | ○ | ○ | ○ |
| | | | X3 | | | | | | | | | | | | | |
| | Concentration in dehydrated THF solution [%] | | | 5 | 5 | 5 | 5 | 5 | 5 | 5 | 5 | 5 | 15 | 15 | 15 | 15 |
| | Drying temperature on tube surface [° C.] | | | — | — | — | 55 | 55 | 55 | 25 | 25 | 25 | — | — | — | 55 |
| | Drying time [min] | | | — | — | — | 60 | 60 | 60 | 60 | 60 | 60 | — | — | — | 60 |
| Y Solution | Dehydrated THF solution of vinyl ether/maleic anhydride copolymer (c) | Mw 2,000,000 | Y1 | ○ | | | ○ | | | ○ | | | ○ | | | ○ |
| | | | Y2 | | ○ | | | ○ | | | ○ | | | ○ | | |
| | | | Y3 | | | ○ | | | ○ | | | ○ | | | ○ | |
| | | Mw 1,000,000 | Y4 | | | | | | | | | | | | | |
| | | | Y5 | | | | | | | | | | | | | |
| | | | Y6 | | | | | | | | | | | | | |
| | Conversion ratio of copolymer (c) [mol %] | | | | | | | | | 1 to 5 | | | | | | |
| | Concentration in dehydrated THF solution [%] | | | 2.5 | 5 | 10 | 2.5 | 5 | 10 | 2.5 | 5 | 10 | 2.5 | 5 | 10 | 2.5 |
| | Drying temperature on tube surface [° C.] | | | — | — | — | 50 | 50 | 50 | 50 | 50 | 50 | — | — | — | 50 |
| | Drying time [min] | | | — | — | — | 60 | 60 | 60 | 60 | 60 | 60 | — | — | — | 60 |
| Z Solution | Coating solution containing 100 parts of Y solution and 5 parts of X solution | | Z1(X1 + Y1) | ○ | | | | | | | | | | | | |
| | | | Z2(X1 + Y2) | | ○ | | | | | | | | | | | |
| | | | Z3(X1 + Y3) | | | ○ | | | | | | | | | | |
| | | | Z4(X2 + Y1) | | | | | | | | | | ○ | | | |
| | | | Z5(X2 + Y2) | | | | | | | | | | | ○ | | |
| | | | Z6(X2 + Y3) | | | | | | | | | | | | ○ | |
| | | | Z7(X3 + Y4) | | | | | | | | | | | | | |
| | | | Z8(X3 + Y5) | | | | | | | | | | | | | |
| | | | Z9(X3 + Y6) | | | | | | | | | | | | | |
| | Drying temperature on tube surface [° C.] | | | 50 | 50 | 50 | | | | | | | 80 | 80 | 80 | |
| | Drying time [min] | | | 60 | 60 | 60 | | | | | | | 60 | 60 | 60 | |
| Evaluation | Appearance | | | ○ | ○ | ○ | ○ | ○ | ○ | ○ | ○ | ○ | ○ | ○ | ○ | ○ |
| | Durability (elastomer portion) | | | ◎ | ◎ | ◎ | ○ | ○ | ○ | ○ | ○ | ○ | ◎ | ◎ | ◎ | ○ |
| | Durability (nylon portion) | | | ○ | ○ | ○ | Δ | Δ | Δ | Δ | Δ | Δ | ○ | ○ | ○ | Δ |

| | | | | Example | | | | | | | | Comparative Example | | |
|---|---|---|---|---|---|---|---|---|---|---|---|---|---|---|
| | | | | 14 | 15 | 16 | 17 | 18 | 19 | 20 | 21 | 1 | 2 | 3 |
| X Solution | Dehydrated THF solution of prepolymer of diisocyanate compound (a) and polyol compound (b) | | X1 | | | | | | | | | | | |
| | | | X2 | ○ | ○ | ○ | ○ | ○ | | | | | | |
| | | | X3 | | | | | | ○ | ○ | ○ | | | |
| | Concentration in dehydrated THF solution [%] | | | 15 | 15 | 15 | 15 | 15 | 10 | 10 | 10 | | | |
| | Drying temperature on tube surface [° C.] | | | 55 | 55 | 25 | 25 | 25 | — | — | — | | | |
| | Drying time [min] | | | 60 | 60 | 60 | 60 | 60 | — | — | — | | | |
| Y Solution | Dehydrated THF solution of vinyl ether/maleic anhydride copolymer (c) | Mw 2,000,000 | Y1 | | | | ○ | | | | | ○ | | |
| | | | Y2 | ○ | | | | ○ | | | | | ○ | |
| | | | Y3 | | ○ | | | | ○ | | | | | ○ |
| | | Mw 1,000,000 | Y4 | | | | | | | ○ | | | | |
| | | | Y5 | | | | | | | | ○ | | | |
| | | | Y6 | | | | | | | | | | | |
| | Conversion ratio of copolymer (c) [mol %] | | | | | | | | 1 to 5 | | | | 1 to 5 | |
| | Concentration in dehydrated THF solution [%] | | | 5 | 10 | 2.5 | 5 | 10 | 2.5 | 5 | 10 | 2.5 | 5 | 10 |
| | Drying temperature on tube surface [° C.] | | | 50 | 50 | 50 | 50 | 50 | — | — | — | 100 | 100 | 100 |
| | Drying time [min] | | | 60 | 60 | 60 | 60 | 60 | — | — | — | 60 | 60 | 60 |

TABLE 3-continued

|  |  |  |  |  |  |  |  |  |  |  |  |  |
|---|---|---|---|---|---|---|---|---|---|---|---|---|
| Z Solution | Coating solution containing 100 parts of Y solution and 5 parts of X solution | Z1(X1 + Y1) Z2(X1 + Y2) Z3(X1 + Y3) Z4(X2 + Y1) Z5(X2 + Y2) Z6(X2 + Y3) Z7(X3 + Y4) Z8(X3 + Y5) Z9(X3 + Y6) | | | | | | | ○ | ○ | ○ | |
|  | Drying temperature on tube surface [° C.] | | | | | | | | 80 | 80 | 80 | |
|  | Drying time [min] | | | | | | | | 60 | 60 | 60 | |
| Evaluation | Appearance | | ○ | ○ | ○ | ○ | ○ | ○ | ○ | ○ | ○ | ○ | △ |
|  | Durability (elastomer portion) | | ○ | ○ | ○ | ○ | ○ | ◎ | ◎ | ◎ | △ | △ | △ |
|  | Durability (nylon portion) | | △ | △ | △ | △ | △ | ○ | ○ | ○ | △ | △ | △ |

TABLE 4

|  |  |  | Example |  |  |  |  |  |  |  |  |  |  |  |  |
|---|---|---|---|---|---|---|---|---|---|---|---|---|---|---|---|
|  |  |  | 22 | 23 | 24 | 25 | 26 | 27 | 28 | 29 | 30 | 31 | 32 | 33 | 34 |
| X Solution | Dehydrated THF solution of prepolymer of diisocyanate compound (a) and polyol compound (b) | X1 | ○ | ○ | ○ | ○ | ○ | ○ | ○ | ○ | ○ | | | | |
|  |  | X2 | | | | | | | | | | ○ | ○ | ○ | ○ |
|  |  | X3 | | | | | | | | | | | | | |
|  | Concentration in dehydrated THF solution [%] | | 5 | 5 | 5 | 5 | 5 | 5 | 5 | 5 | 5 | 15 | 15 | 15 | 15 |
|  | Drying temperature on tube surface [° C.] | | — | — | — | 55 | 55 | 55 | 25 | 25 | 25 | — | — | — | 55 |
|  | Drying time [min] | | — | — | — | 60 | 60 | 60 | 60 | 60 | 60 | — | — | — | 60 |
| Y Solution | Dehydrated THF solution of vinyl ether/maleic anhydride copolymer (c) | Mw 2,000,000 | Y7 | ○ | | | ○ | | | ○ | | | ○ | | | ○ |
|  |  | Y8 | | ○ | | | ○ | | | ○ | | | ○ | | |
|  |  | Y9 | | | ○ | | | ○ | | | ○ | | | ○ | |
|  | Mw 1,000,000 | Y10 | | | | | | | | | | | | | |
|  |  | Y11 | | | | | | | | | | | | | |
|  |  | Y12 | | | | | | | | | | | | | |
|  | Conversion ratio of copolymer (c) [mol %] | | | | | | | 5 to 30 | | | | | | | |
|  | Concentration in dehydrated THF solution [%] | | 2.5 | 5 | 10 | 2.5 | 5 | 10 | 2.5 | 5 | 10 | 2.5 | 5 | 10 | 2.5 |
|  | Drying temperature on tube surface [° C.] | | — | — | — | 50 | 50 | 50 | 50 | 50 | 50 | — | — | — | 50 |
|  | Drying time [min] | | — | — | — | 60 | 60 | 60 | 60 | 60 | 60 | — | — | — | 60 |
| Z Solution | Coating solution containing 100 parts of Y solution and 5 parts of X solution | Z10(X1 + Y7) | ○ | | | | | | | | | | | | |
|  |  | Z11(X1 + Y8) | | ○ | | | | | | | | | | | |
|  |  | Z12(X1 + Y9) | | | ○ | | | | | | | | | | |
|  |  | Z13(X2 + Y7) | | | | | | | | | | ○ | | | |
|  |  | Z14(X2 + Y8) | | | | | | | | | | | ○ | | |
|  |  | Z15(X2 + Y9) | | | | | | | | | | | | ○ | |
|  |  | Z16(X3 + Y10) | | | | | | | | | | | | | |
|  |  | Z17(X3 + Y11) | | | | | | | | | | | | | |
|  |  | Z18(X3 + Y12) | | | | | | | | | | | | | |
|  | Drying temperature on tube surface [° C.] | | 50 | 50 | 50 | | | | | | | 80 | 80 | 80 | |
|  | Drying time [min] | | 60 | 60 | 60 | | | | | | | 60 | 60 | 60 | |
| Evaluation | Appearance | | ○ | ○ | ○ | ○ | ○ | ○ | ○ | ○ | ○ | ○ | ○ | ○ | ○ |
|  | Durability (elastomer portion) | | ◎ | ◎ | ◎ | ○ | ○ | ○ | ◎ | ◎ | ◎ | ◎ | ◎ | ◎ | ○ |
|  | Durability (nylon portion) | | ◎ | ◎ | ◎ | △ | △ | △ | ○ | ○ | ○ | ◎ | ◎ | ◎ | △ |

|  |  |  | Example |  |  |  |  |  |  |  | Comparative Example |  |  |
|---|---|---|---|---|---|---|---|---|---|---|---|---|---|
|  |  |  | 35 | 36 | 37 | 38 | 39 | 40 | 41 | 42 | 4 | 5 | 6 |
| X Solution | Dehydrated THF solution of prepolymer of diisocyanate compound (a) and polyol compound (b) | X1 | | | | | | | | | | | |
|  |  | X2 | ○ | ○ | ○ | ○ | ○ | | | | | | |
|  |  | X3 | | | | | | ○ | ○ | ○ | | | |
|  | Concentration in dehydrated THF solution [%] | | 15 | 15 | 15 | 15 | 15 | 10 | 10 | 10 | | | |
|  | Drying temperature on tube surface [° C.] | | 55 | 55 | 25 | 25 | 25 | — | — | — | | | |
|  | Drying time [min] | | 60 | 60 | 60 | 60 | 60 | — | — | — | | | |
| Y Solution | Dehydrated THF solution of vinyl ether/maleic anhydride copolymer (c) | Mw 2,000,000 | Y7 | | | | ○ | | | | | ○ | | |
|  |  | Y8 | ○ | | | ○ | | | | | | ○ | |
|  |  | Y9 | | ○ | | | ○ | | | | | | ○ |
|  | Mw 1,000,000 | Y10 | | | | | | ○ | | | | | |
|  |  | Y11 | | | | | | | ○ | | | | |
|  |  | Y12 | | | | | | | | ○ | | | |
|  | Conversion ratio of copolymer (c) [mol %] | | | | | | 5 to 30 | | | | | 5 to 30 | |
|  | Concentration in dehydrated THF solution [%] | | 5 | 10 | 2.5 | 5 | 10 | 2.5 | 5 | 10 | 2.5 | 5 | 10 |
|  | Drying temperature on tube surface [° C.] | | 50 | 50 | 50 | 50 | 50 | — | — | — | 100 | 100 | 100 |
|  | Drying time [min] | | 60 | 60 | 60 | 60 | 60 | — | — | — | 60 | 60 | 60 |

TABLE 4-continued

| | | | | | | | | | | | | |
|---|---|---|---|---|---|---|---|---|---|---|---|---|
| Z Solution | Coating solution containing 100 parts of Y solution and 5 parts of X solution | Z10(X1 + Y7) Z11(X1 + Y8) Z12(X1 + Y9) Z13(X2 + Y7) Z14(X2 + Y8) Z15(X2 + Y9) Z16(X3 + Y10) Z17(X3 + Y11) Z18(X3 + Y12) | | | | | | | ○ | ○ | ○ | |
| | Drying temperature on tube surface [° C.] | | | | | | | | 80 | 80 | 80 | |
| | Drying time [min] | | | | | | | | 60 | 60 | 60 | |
| Evaluation | Appearance | | ○ | ○ | ○ | ○ | ○ | ○ | ○ | ○ | ○ | △ |
| | Durability (elastomer portion) | | ○ | ○ | ◎ | ◎ | ◎ | ◎ | ◎ | ◎ | △ | △ | △ |
| | Durability (nylon portion) | | △ | △ | △ | △ | △ | ◎ | ◎ | ◎ | △ | △ | △ |

Examples 43 to 45

Tubes with a coating layer were obtained in the same manner as in Examples 31 to 33 except that a 0.1 to 0.3 N aqueous sodium hydroxide solution warmed at 40° C. was used as the aqueous sodium hydroxide solution for immersing a tube after coating in place of a 0.1 to 1.0 N aqueous sodium hydroxide solution. The appearance and the durability of the obtained tubes were evaluated. Table 5 shows the results.

Examples 46 to 48

Tubes with a coating layer were obtained in the same manner as in Examples 43 to 45 except that the respective coating Y13 to Y15 solutions were used in place of the coating Y7 to Y9 solutions. The appearance and the durability of the obtained tubes were evaluated. Table 5 shows the results.

The invention claimed is:

1. A coating solution comprising:
   a diisocyanate compound (a) selected from the group consisting of aromatic diisocyanates, aliphatic diisocyanates, and alicyclic diisocyanates;
   a polyol (b); and
   a copolymer (c) having a functional group selected from the group consisting of carboxylic acid groups, carboxylic acid ester groups, and carboxylic acid anhydride groups.

2. The coating solution according to claim 1, wherein the coating solution contains the component (a) in an amount of 0.01 to 50% by weight relative to the total amount of all components, the component (b) in an amount of 0.01 to 30% by weight relative to the total amount of all components, and the component (c) in an amount of 40 to 99% by weight relative to the total amount of all components.

3. The coating solution according to claim 1 or 2, wherein the number of moles of all isocyanate groups in the component (a) is larger than the number of moles of all hydroxy groups in the component (b).

4. The coating solution according to claim 1, wherein the component (c) is a copolymer containing a maleic anhydride unit having a maleic anhydride group.

TABLE 5

| | | | Example | | | | | |
|---|---|---|---|---|---|---|---|---|
| | | | 43 | 44 | 45 | 46 | 47 | 48 |
| X Solution | Dehydrated THF solution of prepolymer of diisocyanate compound (a) and polyol compound (b) | X1 X2 X3 | ○ | ○ | ○ | ○ | ○ | ○ |
| | Concentration in dehydrated THF solution [%] | | 15 | 15 | 15 | 15 | 15 | 15 |
| Y Solution | Dehydrated THF solution of vinyl ether/maleic anhydride copolymer (c)(Mw 2,000,000) | Y7 Y8 Y9 Y13 Y14 Y15 | ○ | ○ | ○ | ○ | ○ | ○ |
| | Conversion ratio of copolymer (c) [mol %] | | 5 to 30 | | | 60 to 70 | | |
| | Concentration in dehydrated THF solution [%] | | 2.5 | 5 | 10 | 2.5 | 5 | 10 |
| Z Solution | Coating solution containing 100 parts of Y solution and 5 parts of X solution | Z13(X2 + Y7) Z14(X2 + Y8) Z15(X2 + Y9) Z19(X2 + Y13) Z20(X2 + Y14) Z21(X2 + Y15) | ○ | ○ | ○ | ○ | ○ | ○ |
| | Drying temperature on tube surface [° C.] | | 80 | 80 | 80 | 80 | 80 | 80 |
| | Drying time [min] | | 60 | 60 | 60 | 60 | 60 | 60 |
| Evaluation | Appearance | | ○ | ○ | ○ | ○ | ○ | ○ |
| | Durability (elastomer portion) | | ◎ | ◎ | ◎ | ◎ | ◎ | ◎ |
| | Durability (nylon portion) | | ◎ | ◎ | ◎ | ◎ | ◎ | ◎ |

5. The coating solution according to claim 1, wherein the component (c) is a vinyl ether/maleic anhydride copolymer containing a vinyl ether unit and a maleic anhydride unit having a maleic anhydride group.

6. The coating solution according to claim 1, wherein the coating solution contains a prepolymer prepared by previously reacting at least some of the component (a) with at least some of the component (b) or the component (c).

7. The coating solution according to claim 1, wherein in the component (c), at least a part of the carboxylic acid ester group and the carboxylic acid anhydride group is converted into the carboxylic acid group.

8. The coating solution according to claim 7, wherein 1 mol % or more and 100 mol % or less of the total amount of the carboxylic acid ester group and the carboxylic acid anhydride group is converted into the carboxylic acid group.

9. The coating solution according to claim 1, wherein the coating solution is a non-aqueous solution.

10. A method for forming a coating layer, the method comprising:
   applying the coating solution according to claim 1 to at least a part of an object; and
   drying the coating.

11. The method for forming a coating layer according to claim 10, wherein the coating solution having a solution temperature of 40° C. or less is applied to the object.

* * * * *